United States Patent [19]
Wenzhi

[11] Patent Number: 5,484,733
[45] Date of Patent: Jan. 16, 1996

[54] METHOD FOR DIAGNOSING RHEUMATISM

[75] Inventor: Hu Wenzhi, Nagoya, Japan

[73] Assignee: Soichi Inoue, Japan

[21] Appl. No.: 108,289

[22] Filed: Aug. 19, 1993

[30] Foreign Application Priority Data

Apr. 5, 1993 [JP] Japan .................................. 5-103626

[51] Int. Cl.$^6$ ................................................. G01N 30/02
[52] U.S. Cl. ........................ 436/161; 210/656; 210/660; 436/63; 436/174
[58] Field of Search ........................... 436/161, 63, 174; 422/70; 73/61.52, 61.53, 61.55; 210/656, 660, 198.2

[56] References Cited

U.S. PATENT DOCUMENTS

| | | | |
|---|---|---|---|
| 3,689,632 | 9/1972 | Mizushima et al. | 424/12 |
| 4,992,531 | 2/1991 | Patroni et al. | 530/351 |
| 5,032,503 | 7/1991 | Khanna et al. | 435/7.6 |
| 5,034,316 | 7/1991 | Weisbart et al. | 435/7.24 |
| 5,245,008 | 9/1993 | Dickhardt et al. | 530/305 |

OTHER PUBLICATIONS

Bennington et al, Saunders Dictionary & Encyclopedia of Laboratory Medicine and Technology, W.B. Saunders Co 1984 pp. 1329–1331.

Nomura et al. Analytical Chemistry, vol. 60, pp. 2509–2512, 1988.

Kurganov et al. Journal of Chromatography, vol. 548, pp. 207–214, 1991.

Tranposch et al. Journal of Chromatography, vol. 544, pp. 113–123, 1990.

Zlatkis et al. Clinical Chemistry, vol. 27/6, pp. 789–797, 1981.

Hu et al. Bulletin Chemical Society of Japan, vol. 66, No. 5, pp. 1420–1423, May 1993.

Hu et al. Analytical Chemistry, vol. 65, pp. 2204–2208, Sep. 1, 1993.

Tellerova et al. Journal of Chromatography, vol. 273, pp. 197–201, 1983.

Lempiäinen et al. Journal of Chromatography, vol. 341, pp. 105–113, 1985.

*Primary Examiner*—James C. Housel
*Assistant Examiner*—Jan M. Ludlow
*Attorney, Agent, or Firm*—Finnegan, Henderson, Farabow, Garrett & Dunner

[57] ABSTRACT

The present invention relates to a rapid, simple and reliable method and a device for diagnosing rheumatism under no influence of diet. The method for diagnosing rheumatism includes injecting the urine sample from a suspected case of rheumatism into one end of a solid phase packed in a separation column 3, thereafter eluting a phosphate buffer as an eluent to separate the analytes contained in the urine sample, subsequently detecting the individual separated analytes with a detector 4 to confirm that a predetermined chromatogram is demonstrated by liquid chromatography, the chromatogram developing a higher chromato-peak of the rheumatism-specific component contained in the urine of the patient compared with a chromato-peak of non-rheumatic individual, and establishing the diagnosis of rheumatism on the basis of the presence of the higher peak, wherein a negative/positive charged micellar stationary phase is employed as the stationary phase, including a support carrier and a zwitterionic layer formed by directly or indirectly coating CHAPS and/or CHAPSO micelle on the surface of the support carrier.

6 Claims, 6 Drawing Sheets

METHOD FOR DIAGNOSING RHEUMATISM

BACKGROUND OF THE INVENTION

1. Field of the Invention

The present invention relates to a method for diagnosing rheumatism and a device therefor. The present invention can be applied in various manners to clinical diagnosis and the like, requiring rapidness and accuracy.

2. Prior Art

Diagnosis of rheumatoid factor such as IgG, IgM, IgA, and IgE in serum by RA Test, RAHA Test are the prior common clinical method for the diagnosis of rheumatism.

3. Problems to be Solved by the Invention

However, for the chronic rheumatic individual, only 70–80% can be qualified by such as these methods.

It has not been known any methods using liquid chromatography to diagnose the presence or absence of rheumatism.

SUMMARY OF THE INVENTION

Object of the Invention

By overcoming the above drawbacks, the object of the present invention is to provide a rapid, simple and reliable method for diagnosing rheumatism under no influence of diet, together with a device therefor.

Characteristics of the Invention

The method for diagnosing rheumatism in accordance with the present invention comprises injecting the urine sample from a suspected case of rheumatism into one end of a solid phase packed in a separation column, thereafter eluting a phosphate buffer as an eluent to separate the analytes contained in the urine sample, subsequently detecting the individual separated analytes to confirm that a predetermined chromatogram is demonstrated by liquid chromatography, the chromatogram developing a higher chromato-peak of the rheumatism-specific component comparing with a chromato-peak of the individual of non-rheumatism, and establishing the diagnosis of rheumatism on the basis of the presence of the, peak, wherein a zwitterionic stationary phase is employed as the stationary phase, comprising a support carrier and a negative/positive-charged layer formed by directly or indirectly coating a compound ;3-[(3-Cholamidepropyl)dimethyl ammonio]-1-propanesulfonate (referred to as "CHAPS") and/or a compound ;3-[(3-Cholamidepropyl)dimethyl ammonio]-2-hydroxy-1-propanesulfonate (referred to as "CHAPSO"), on the surface of the support carrier.

The device for diagnosing rheumatism in accordance with the present invention comprises an eluent feeding pump, a separation column connected to the pump, a UV detector for detecting the analytes separated through the separation column, a recording device recording the results of the separation, and an urine sample injector to inject the urine sample from a suspected case of rheumatism into a connecting tube connected in between the separation column and the pump, wherein the separation column is packed with a negative/positive-charged stationary phase comprising a support carrier and a negative/positive-charged layer formed by directly or indirectly coating CHAPS and/or CHAPSO, on the surface of the support carrier, characterized in that the recording device records the presence of a higher chromato-peak of the component specific to rheumatism compared with a chromato-peak of non-rheumatism, if any, thereby establishing the diagnosis of rheumatism.

Effect of the Invention

According to the method and device in accordance with the present invention, the higher chromato-peak of the component specific to rheumatism can be detected well, so that the diagnosis of rheumatism can be established based on the presence of the higher specific peak, in rapid, simple and accurate manners with no influence of diet.

DETAILED DESCRIPTION OF THE INVENTION

In accordance with the present invention, a support carrier of any material, form or size may be used in the aforementioned "negative/positive-charged stationary phase", without any specific limitation, if a zwitterionic layer can be formed on the surface of the carrier. The material is illustrated, for example, by silica gel, polystyrene and the like, and the surface thereof is preferably porous for ready immobilization. Furthermore, the zwitterionic layer may directly be formed on a carrier to be used, through chemical reaction or physical adsorption; a zwitterionic layer may be formed on the surface of the carrier through a hydrophobic layer being formed thereon as an adhesive layer (in other words, indirectly formed on the surface of the carrier).

For example, a carrier comprises porous silica gel the aforementioned "zwitterionic stationary phase"; on the surface of the carrier is formed a hydrophobic layer obtained through alkylsilane reaction; and furthermore, the zwitterionic layer is adsorbed and formed onto the surface of the hydrophobic layer. The alkyl group of the alkylsilane is preferably the one with about 12 to 24 carbon atoms so as to provide hydrophobicity; the one with 18 carbon atoms is employed in general.

The term "eluent" (sometimes referred to as "mobile phase") means a phosphate buffer containing a phosphate salt and having a buffer action. As the buffer, a variety of known phosphate salts ($NaH_2PO_4+Na_2HPO_4$, $NaH_2PO_4+$ citric acid, $NaH_2PO_4+NaHCO_3$, etc.) may generally be used with purified water and the like as a solvent, without limitation. Any solvent which can dissolve the phosphate salts can be used. Any ion concentration may he selected therefor.

As the "means" to detect the separated analyte components, an ultraviolet (referred to as "IV" hereinbelow) detector may be used without limitation; other known means (electric conductivity detector or electrochemical detector) may be used as well. And there may be used an UV detector, because the analytes in the urine samples from rheumatic and non-rheumatic individuals (particularly, the specific component) have a UV absorption range of about 200 to 260 nm.

Embodiment

The present invent ion will now be explained in details with reference to examples.

(1) Liquid Chromatography Device and Conditions Therefor

Figure 1:
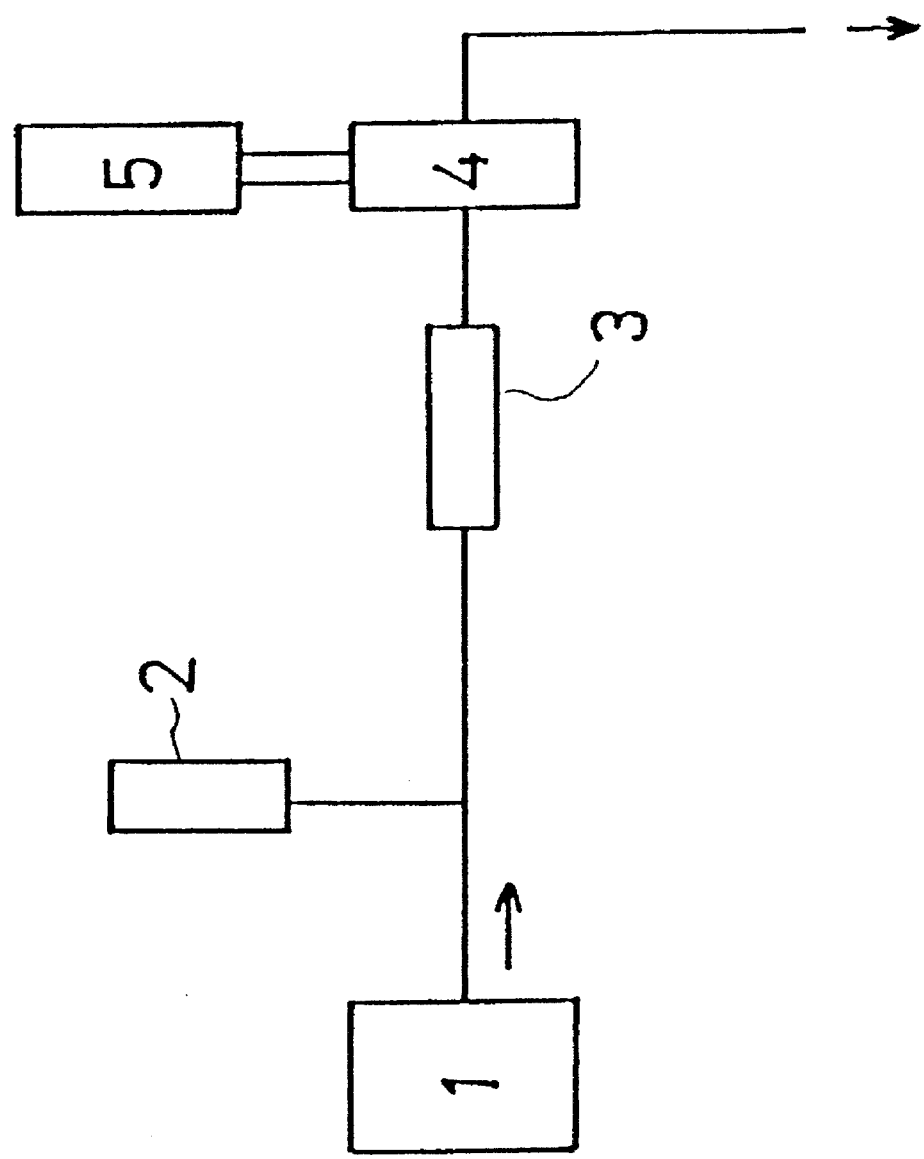
FIG. 1 is a schematic explanatory view of the device used in Example for diagnosing rheumatism.

As shown in FIG. 1, the present device comprises an eluent feeding pump 1, a separation column 3 connected to the pump 1, a UV detector 4 for detecting the analytes separated through the separation column 3, a recording device 5 recording the results of the separation, and a liquid sample injector 2 to inject an urine sample into a connecting tube connected in between the separation column 3 and the pump 1.

Figure 2:
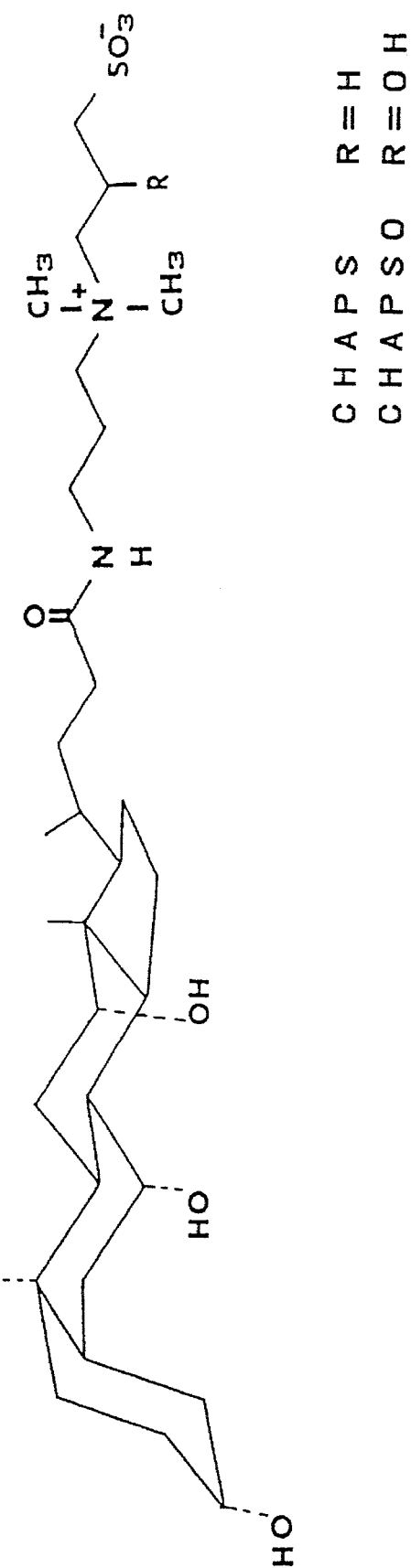
FIG. 2 is an explanatory view depicting the chemical structures of CHAPS and CHAPSO.

As such pump 1, "LC-6A" pump (manufactured by Shimadzu Seisakusho Corporation) was used. As such sample injecting part 2, a valve ("LC-6A" as product name; manufactured by Shimadzu Seisakusho Corporation; injection volume, 20 µl) was used. As such separation column 3, "L-column" (250 mm×4.6 mm in internal diameter, manufactured by Kagakuhin Kensa Kyokai) was used. As shown in FIG. 2, subsequently, "CHAPS" (manufactured by Dojin Corporation, zwitterionic surfactant; depicted in FIG. 2) or "CHAPSO" (manufactured by Dojin Corporation, zwitterionic surfactant; depicted in FIG. 2), was immobilized (coated) onto the surface of the ODS carrier (prepared by reacting a carrier of porous silica gel with octadecyl silane (ODS), and comprises the carrier and the ODS layer) to prepare negative/positive-charged stationary phase.

The method for immobilization is as follows. An aqueous 30 mmol/liter micellar solution, as a predetermined surfactant (CHAPS or CHAPSO) passed through a column packed with the ODS carrier at a flow rate of 0.7 ml/min for 40 minutes. The concentration of the surfactant should be higher than the critical micelle concentration (CMC).

A UV detector (detection wave length of 215 nm, manufactured by Shimadzu Seisakusho Corporation) with a flow cell was used as a UV detector 4; "Chromatopack C-R4AX Data Processor" (as product name; manufactured by Shimadzu Seisakusho Corporation) was used as a recording device 5. A aqueous buffer solution of phosphate salts ($NaH_2PO_4$: 10 mmol/liter+$Na_2HPO_4$: 10 mmol/liter) as an eluent (mobile phase) was used, and this flow rate was 0.7 ml/min., the separation was done at room temperature.

(2) Separation of Urine Sample and Diagnosis of Rheumatism

The following experiments were done with the above device under the above conditions.

Figure 4:
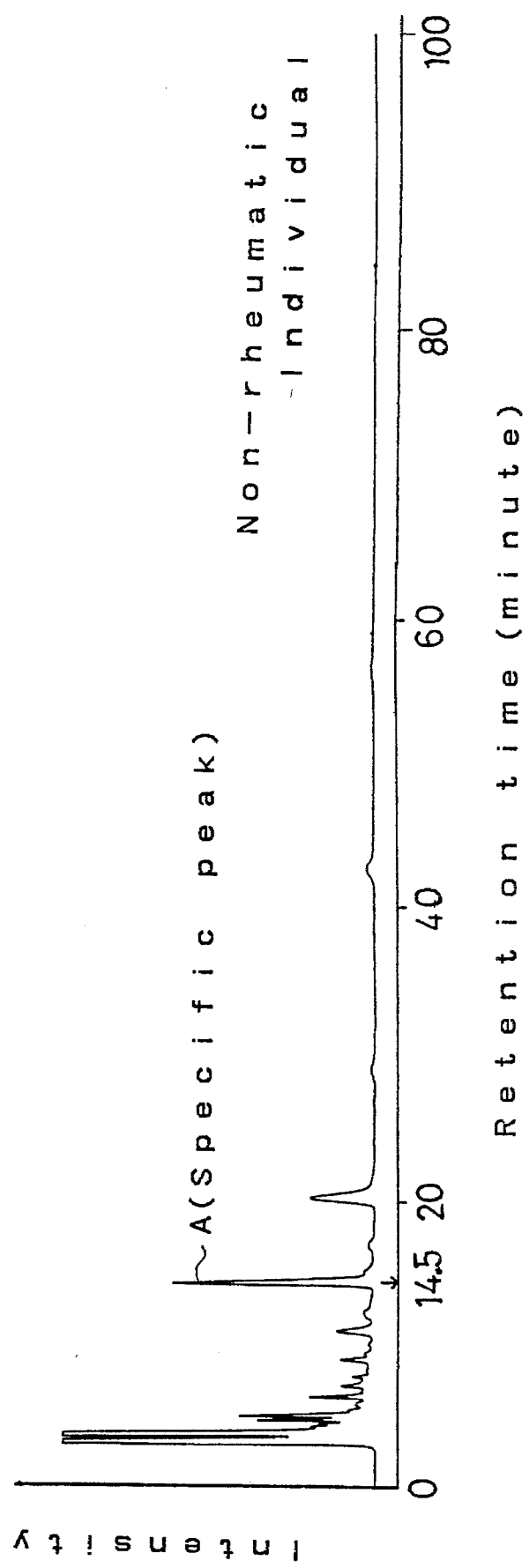
FIG. 4 is an explanatory view depicting the chromatogram from the analysis of the urine sample from a non-rheumatic individual in Example.

For the separation of urine samples, urine sample was diluted to two-fold with pure water, and 20 µl of this sample was injected into the present system. A chromatogram of urine sample obtained by using CHAPS micelle coated stationary phase with phosphate buffer as the mobile phase is shown in FIG. 4. As can be seen in FIG. 4, the mean components in human urine were eluted within about 20 min., and all of the components were eluted within 55 min. The urine sample was also separated by using conventional ODS stationary phase, 3 hours were required for resolution of the mean components, and for the resolution of the all of the components, 2 days were required. Therefore, the conventional components can be separated in shorter time by the use of the zwitterionic micellar stationary phase compared with ODS solid phase.

Figure 3:
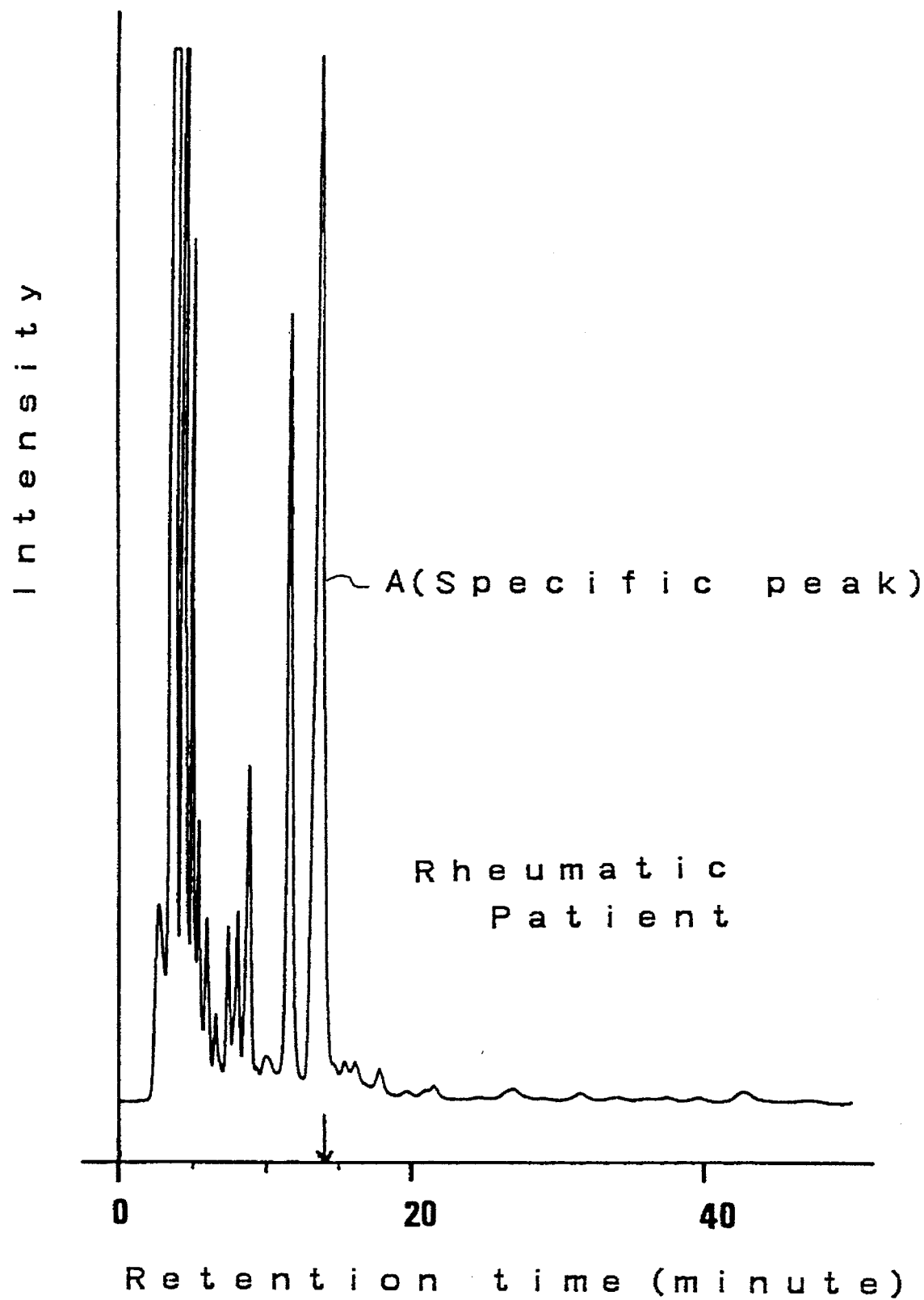
FIG. 3 is an explanatory view depicting the chromatogram from the analysis of the urine sample from a rheumatic patient in Example.

Furthermore, we have found that the concentration of a compound (called peak A) eluted at 14.5 min was much higher than that found in non-rheumatic urine. For the further test, 60 urine samples obtained from the rheumatic individuals and 40 urine samples obtained from non-rheumatic individuals were also examined. The concentration of the compound (peak A) was 2–10 times higher in the all of the urine samples from the rhematic individuals (FIG. 3). For one example, the chromatogram of a certain rheumatic patient among them, is shown in FIG. 3; that of a non-rheumatic patient is shown in FIG. 4.

Figure 5:
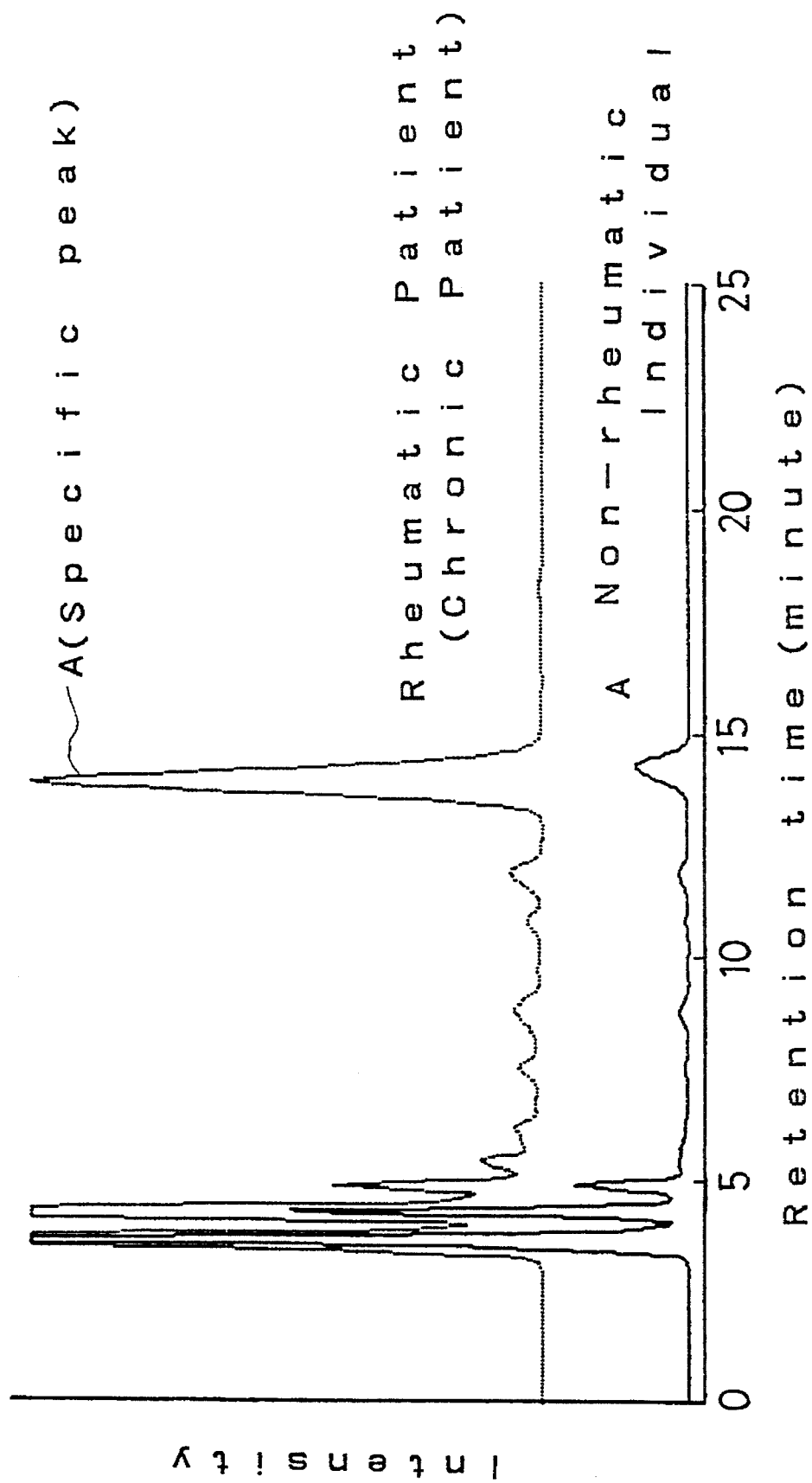
FIG. 5 is an explanatory view depicting the chromatogram from the analysis of the urine samples from the rheumatic patient (a chronic patient) and the non-rheumatic individual in Example.
Figure 6:
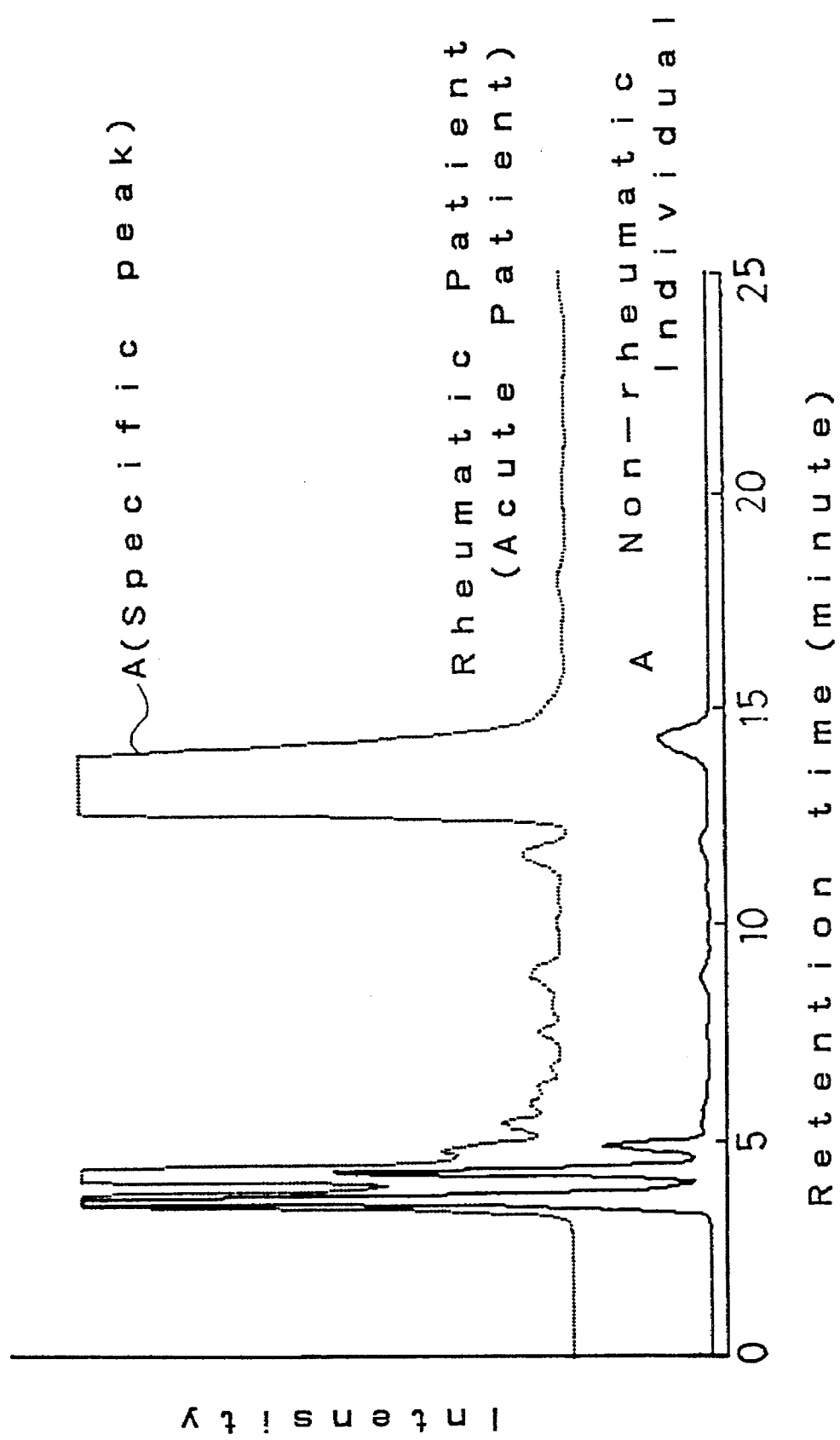
FIG. 6 is an explanatory view depicting the chromatogram from the analysis of the urine samples from the rheumatic patient (a acute patient) and the non-rheumatic individual in Example.

Furthermore, the individual chromatograms from a rheumatic patient (FIG. 5; a chronic patient, FIG. 6; a acute patient) and a non-rheumatic patient were recorded together in FIGS. 5–6. The rheumatic patient's chromatogram and the non-rheumatic patient's chromatogram of FIG. 5 and FIG. 6 were measured by same sensibility. Even in the figures, the intensity of specific-peak A having the 14.5-min. retention time which appears on the chromatogram of the rheumatic patient is much greater than the intensity of specific-peak which appears on the chromatogram of the non-rheumatic patient.

No diet control was imposed to the great number of the rheumatic or non-rheumatic individuals; sample collection was done after diet, prior to diet or after the intake of drinks; and collection time had variation, such as in the morning or in the afternoon.

Thus, a liquid chromatography method using CHAPS micellar stationary phase can establish the diagnosis of rheumatism in such a simple and reliable manner. The present method is not under the influence of the intake of diet, with the results of better reliability on the diagnosis and more advantage to testing personnel.

In addition, the same result (not shown in Fig.) as use of CHAPS was also shown in use of CHAPSO as a substitute for CHAPS. The same urine samples were also analyzed by using the ODS stationary phase (not covered by CHAPS or CHAPSO) liquid chromatography, however, the compound (peak A) was not founded.

In accordance with the present invention, various modification may be possible depending on the objective and the use within the scope of the present invention, without limitation to the specific example described above. That is, the chromatogram was used visually in the above example for diagnosis, without limitation. For example, the presence of the chromato-peak of the component specific to rheumatism may be read mechanically (automatically) for diagnosis. In such case, the outcome of the diagnosis may be represented with a lamp or the like.

What is claimed is:

1. A method for aiding in diagnosing rheumatism in an individual suspected of having rheumatism, which method comprises:

(a) subjecting each of a first urine sample from said individual and at least one second urine sample from a non-rheumatic patient to liquid chromatography to separate each of said samples into its component parts employing a (i) negative/positive charged micellar stationary phase comprising a support carrier and a zwitterionic layer formed by directly or indirectly coating a compound selected from the group consisting of 3-[(3-Cholamidepropyl)dimethyl ammonio]-1-propanesulfonate and 3[(3-Cholamidepropyl)dimethyl ammonio]-2-hydroxy-1-propane-sulfonate on the surface of the support carrier and (ii) a mobile phase comprising an aqueous solution of a phosphate buffer;

(b) detecting the resulting separated components in each of said samples;

(c) determining a first concentration of specific component detected in said first urine sample and a second concentration of said specific component detected in said second urine sample, which specific component is peak A of FIG. 3;

(d) comparing said first concentration with said second concentration; and (e) using the comparison of said first and said second concentrations to aid in diagnosing rheumatism in said individual.

2. The method of claim 1, wherein the carrier comprises porous silica gel; a hydrophobic layer generated via alkylsilane reaction is formed on the surface of the carrier; and the zwitterionic layer is absorbed and formed onto the surface of the hydrophobic layer.

3. The method of claim 1, further including producing a chromatogram of said detected components and wherein a first chromato-peak of the specific component in the urine of said individual suspected of having rheumatism is compared with a second chromato-peak of the urine of a non-rheumatic individual, said first and second chromato-peaks occurring at the same retention time.

4. The method of claim 1, wherein step (b) comprises passing the resulting separated components to an ultraviolet detector for detecting the separated components.

5. In the analysis of urine by the liquid chromatographic separation of a urine sample into its component parts by the use of a mobile phase passed through a separation column packed with a stationary phase, the improved method which comprises:

(a) subjecting a urine sample from an individual to liquid chromatography to separate said sample into its component parts employing a (1) negative/positive charged micellar stationary phase comprising a support carrier and a zwitterionic layer formed by directly or indirectly coating a compound selected from the group consisting of 3-[(3-Cholamidepropyl)dimethyl ammonio]-1-propanesulfonate and 3-[(3-Cholamidepropyl)dimethyl ammonio]-2-hydroxy-1-propanesulfonate on the surface of the support carrier and (2) a mobile phase comprising an aqueous solution of a phosphate buffer; and (b) detecting the concentrations of the resulting separated components.

6. The method of claim 5 wherein the carrier comprises porous silica gel; a hydrophobic layer generated via alkylsilane reaction is formed on the surface of the carrier; and the zwitterionic layer is absorbed and formed onto the surface of the hydrophobic layer.

\* \* \* \* \*